(12) United States Patent
Ou et al.

(10) Patent No.: US 10,912,465 B2
(45) Date of Patent: Feb. 9, 2021

(54) CARDIAC FUNCTION EVALUATION SYSTEM

(71) Applicant: Organ Transport PTY LTD, North Adelaide (AU)

(72) Inventors: Ruchong Ou, Melbourne (AU); John Woodard, Turramurra (AU); Jonathan Cavendish Nevile, Melbourne (AU)

(73) Assignee: Organ Transport PTY LTD, North Adelaide (AU)

( * ) Notice: Subject to any disclaimer, the term of this patent is extended or adjusted under 35 U.S.C. 154(b) by 641 days.

(21) Appl. No.: 14/891,908

(22) PCT Filed: May 26, 2014

(86) PCT No.: PCT/AU2014/000550
§ 371 (c)(1),
(2) Date: Nov. 17, 2015

(87) PCT Pub. No.: WO2014/197924
PCT Pub. Date: Dec. 18, 2014

(65) Prior Publication Data
US 2016/0106323 A1 Apr. 21, 2016

(30) Foreign Application Priority Data
Jun. 14, 2013 (AU) .............................. 2013902151

(51) Int. Cl.
*A61B 5/02* (2006.01)
*A61B 5/00* (2006.01)
(Continued)

(52) U.S. Cl.
CPC ............ *A61B 5/02028* (2013.01); *A01N 1/02* (2013.01); *A01N 1/0242* (2013.01);
(Continued)

(58) Field of Classification Search
CPC . A61B 5/02028; A61B 5/6858; A61B 5/1107; A61B 5/0215; A61B 5/6853;
(Continued)

(56) References Cited

U.S. PATENT DOCUMENTS 4,314,550 A 2/1982 Apstein
5,025,786 A * 6/1991 Siegel ................ A61B 5/02158
600/375

(Continued)

FOREIGN PATENT DOCUMENTS

EP 0425696 A1 5/1991
EP 0471029 A1 2/1992
(Continued)

OTHER PUBLICATIONS

Weber, et al., "Measurement of Ventricular Function in the Experimental Laboratory.", "The Heart and Cardiovascular System: Scientific Foundations", 1986, pp. 865-886, vol. 2, Publisher: Raven Press, New York.*

(Continued)

*Primary Examiner* — Navin Natnithithadha
*Assistant Examiner* — Andrey Shostak
(74) *Attorney, Agent, or Firm* — Kaplan Breyer Schwarz, LLP

(57) ABSTRACT

A device adapted for determining cardiac viability, wherein said device includes: a cannula having a hollow body and at least a distal end adapted for insertion into a heart and operator end for adapted for an operator to position the catheter in the ventricular apex and adapted for connection to a plumbing system; an inflatable balloon positioned near to the distal end in fluid communication with the hollow body to allow for selected inflation of the balloon, a controller adapted to calculate the viability of the heart from (Continued)

pressure data detected within cannula or balloon which is inflated to various degrees with an incompressible fluid.

11 Claims, 7 Drawing Sheets

(51) Int. Cl.
  *A61B 5/0215* (2006.01)
  *A61B 5/11* (2006.01)
  *A01N 1/02* (2006.01)

(52) U.S. Cl.
  CPC .......... *A61B 5/0215* (2013.01); *A61B 5/1107* (2013.01); *A61B 5/6853* (2013.01); *A61B 5/6858* (2013.01); *A61B 5/1108* (2013.01); *A61B 5/1109* (2013.01); *A61B 2562/0247* (2013.01)

(58) Field of Classification Search
  CPC .......... A61B 5/1108; A61B 2562/0247; A61B 5/1109; A01N 1/0242; A01N 1/02
  See application file for complete search history.

(56) References Cited

U.S. PATENT DOCUMENTS

| | | | | |
|---|---|---|---|---|
| 5,181,518 | A | * | 1/1993 | McDonagh ............ G09B 23/28 600/16 |
| 5,431,628 | A | * | 7/1995 | Millar .................. A61B 5/0215 600/470 |
| 5,865,801 | A | * | 2/1999 | Houser .................. A61B 5/036 600/488 |
| 6,100,082 | A | | 8/2000 | Hassanein |
| 2003/0036707 | A1 | | 2/2003 | Holzgrefe |
| 2005/0049509 | A1 | * | 3/2005 | Mansour ............. A61B 5/1076 600/476 |
| 2005/0203425 | A1 | * | 9/2005 | Langston ............. A61B 5/0215 600/485 |
| 2006/0293739 | A1 | * | 12/2006 | Vijay ............... A61B 17/12022 607/122 |
| 2008/0015466 | A1 | * | 1/2008 | Lerman .................. A61B 10/06 600/567 |
| 2009/0137968 | A1 | * | 5/2009 | Rottenberg ........... A61M 29/02 604/264 |
| 2012/0226340 | A1 | | 9/2012 | Leschinsky |
| 2012/0277785 | A1 | | 11/2012 | Aggerholm et al. |
| 2012/0310333 | A1 | | 12/2012 | Bachman |
| 2013/0184515 | A1 | * | 7/2013 | Ovil .................... A61M 1/1086 600/17 |

FOREIGN PATENT DOCUMENTS

| | | |
|---|---|---|
| EP | 2376011 A1 | 10/2011 |
| WO | 2007119241 A1 | 10/2007 |
| WO | 2009055435 A1 | 4/2009 |

OTHER PUBLICATIONS

"International Search Report", issued by the AU Patent Office as International Searching Authority for International Application PCT/AU2014/000550, dated Jul. 8, 2014.

Larson, et al., "Assessment of left ventricular compliance during heart preservation", "Perfusion", 1998, pp. 67-75, vol. 13, Publisher: Arnold, Published in: US.

Ozeki, et al., "Heart Preservation Using Continuous Ex Vivo Perfusion Improves Viability and Functional Recovery", "Circulation Journal", Feb. 2007, pp. 153-159, vol. 71.

Y. Goto et al., "Similar normalized Emax and O2 consumption-pressure-volume area relation in rabbit and dog", "American Journal of Physiology—Heart and Circulatory Physiology", Aug. 1, 1988, H366-H374, vol. 25, Issue 2, https://doi.org/10.1152/ajpheart.1988.255.2.H366.

Robert M. Bell et al., "Retrograde heart perfusion: The Langendorff technique of isolated heart perfusion", "Journal of Molecular and Cellular Cardiology", Jun. 1, 2011, Publisher: Elsevier Ltd., pp. 940-950, vol. 50, Issue 6, DOI: https://doi.org/10.1016/j.yjmcc.2011.02.018.

Hiroyuki Suga et al., "Instantaneous Pressure-Volume Relationships and Their Ratio in the Excised, Supported Canine Left Ventricle", "Circulation Research", Jul. 1, 1974, pp. 117-126, vol. 35.

Eaton, LW et al., "Accurate volume determination in the isolated ejecting canine left ventricle by two-dimensional echocardiography", "Circulation", Aug. 1, 1979, pp. 320-326, 60(2).

* cited by examiner

CARDIAC FUNCTION EVALUATION SYSTEM

TECHNICAL FIELD

The present invention relates to a device or system that comprises a specialised catheter for insertion into the ventricles of a human donor heart. This device or system is adapted to aid surgeons, clinicians and others in regard to conducting heart transplant operations.

BACKGROUND

There has been a long felt need for a system or device that is able to accurately assess the cardiac function of a donor heart and predict the likely post-transplant cardiac function of a donor heart. Preferably, the cardiac function of the donor heart may be measured after transport to the implanting operating room prior to implantation into a recipient patient. Such an evaluation could be performed in an ex vivo situation where the heart is artificially nourished outside the body in a technique commonly known as a Langendorff preparation (see Bell R M et al—J Mol Cell Cardiol 2011, June; 50(6):940-50).

The heart functions effectively as two pumps and either of these two pumps may suffer independent dysfunction. It is therefore desirable to be able to measure the function of each ventricle separately.

Further there has also been a need when using such a device or system in a heart in which the ventricles are not fully filled with blood that prevents air being ejected from the ventricle through the aortic valve, the coronary ostia and thence the coronary arteries with resultant damage to the cardiac muscle.

In addition, it has been necessary to surgically fix the measuring apparatus to the heart in order to prevent the measuring apparatus from being ejected from the ventricular cavity during contraction (see Eaton L W et al. Circulation. 1979; 60:320-326 page 322). Such fixation is laborious and may result in transient or permanent damage to the heart tissues.

The scientific paper Suga H, Sagawa S. Circ Res. 1974: 35:117-126 describes a system for measuring cardiac efficiency in canines. This disclosure is of limited application and is not usable in cardiac transplantation under surgical conditions for humans.

The scientific paper Goto et al, Am J Physiol Heart Circ. Physiol 1988:255:H394-H396 describes a system for measuring the cardiac efficiency of small animals such as rabbits. This disclosure has limited application and is not usable in cardiac transplantation under surgical conditions in humans. Further the analysis completed by this system is limited to volumetric analysis rather than pressure analysis.

Cannulae or catheters have been previously used in cardiac surgery for various uses. US Published Patent Application 20120310333 describes a catheter device for installing a replacement mitral valve.

European Patent 0425696 describes a catheter device with an inflatable balloon attached to the distal end and wherein the balloon is adapted to force open a fused and diseased valve.

European Patent 2376011 describes a catheter device for repairing the mitral valve. The catheter of this disclosure includes an inflatable balloon at a distal end for fixing the catheter in the correct position, the catheter then uses an ultrasonic emitter to the correct and repair the mitral valve.

European Patent 471029 describes a balloon catheter which may be inserted into the left ventricle of the heart. The catheter includes an inflatable balloon positioned at the distal end of the catheter as well as a series of inlet holes. The inlet hoes are positioned so as to provide an inlet for a left ventricle assist device (LVAD) or pump when connected and in use. The balloon aids in positioning and anchoring of the catheter as well as preventing collapse of the left ventricle when low pressures are experienced due to the pumping action of the attached LVAD.

US Published Patent Application 20120226340 describes balloon catheter adapted for placing and positioning a micro axial blood pump in the aorta. The distal end of the catheter includes a balloon which when inflated expands a stenting mesh to engage the inner wall of the blood vessel and anchor the blood pump in place in the blood vessel.

US Published Patent Application US20030036707 describes a method of measuring ventricular function using a unspecialised unspecialized balloon and a series of valves. This disclosure fails to detail in sufficient detail the functioning and features of balloon cannula. In essence, it is a repeat of the above described Langendorff method or technique, which is of limited application for small animal experimental usage and is not usable in cardiac transplantation under surgical conditions for humans.

SUMMARY

Problems to be Solved

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

Means for Solving the Problem

A first aspect of the present invention relates to a device adapted for determining cardiac viability, wherein said device includes: a cannula having a hollow body and at least a distal end adapted for insertion into a heart and operator end for adapted for holding the catheter and positioning the tip within the ventricle; the operator end is adapted for connecting to a plumbing system and pressure transducer; an inflatable balloon positioned near to the distal end in fluid communication with the hollow body to allow for selected inflation of the balloon, a controller adapted to calculate the viability of the heart from pressure data detected within cannula or balloon. The preferred distal end is joined to a pigtail or a blunt bulb shaped arrangement to prevent injury to heart during insertion.

Preferably, the distal end is adapted to be inserted within a ventricle of the heart. The preferred pressure data is calculated from the difference of internal pressure applied to body and balloon by an operator via a syringe or other means of altering the fluid volume and the pressure applied by the interior pressure of the heart acting on the balloon in use and further preferably the pressure data is detected by a pressure sensor in communication with the interior of the balloon.

The balloon may include an expansion limitation to prevent or limit over expansion of the balloon, in use. Preferably, the balloon is attached to the body by tethering in an annulus around the catheter at a position proximal to the distal point. Such an arrangement limits the extent to which the inflated balloon can move relative to the catheter shaft.

The balloon can be made intentionally smaller than the smallest ventricular cavity in which it is used. With the catheter tip positioned at the ventricular apex, this means that the tethered balloon cannot herniate into the atrial cavity when fully inflated.

An expandable cage may be joined to the body in a position adapted to engage the mitral or tricuspid valve when in use and to render it incompetent and thus prevent ventricular fluid contents (including air) being ejected during ventricular contraction through the outlet valve (either aortic valve in the case of the left ventricle or the pulmonary valve in the case of the right ventricle).

Preferably, the hollow body includes a first and second tubes which are integrally joined and parallel. The second tube may include a number of vent holes, the more distal of which will lie in the ventricular cavity and the more proximal will lie in the atrial cavity. The effect of these holes is to render mitral or tricuspid valve ineffective and thus prevent ventricular fluid contents (including air) being ejected during ventricular contraction through the outlet valve (either aortic valve in the case of the left ventricle or the pulmonary valve in the case of the right ventricle).

A second aspect of the present invention may relate to a system adapted for determining cardiac viability, wherein said device includes: a cannula having a hollow body and at least a distal end adapted for insertion into a heart and operator end for adapted for a surgeon or an operator; an inflatable balloon positioned near to the distal end in fluid communication with the hollow body to allow for selected inflation of the balloon, a controller adapted to calculate the viability of the heart from pressure data detected within cannula or balloon and the associated volume data from inflating the balloon.

The preferred distal end is adapted to be inserted within a left or right ventricle of the heart. The preferred pressure data is calculated from the difference of internal pressure applied to body and balloon by a surgeon and the pressure applied by the interior pressure of the heart acting on the exterior surface of the balloon in use.

The pressure data may be detected by a pressure sensor in communication with the interior of the body or balloon.

Preferably, the balloon may include an expansion limitation to prevent or limit over expansion of the balloon, in use. The preferred balloon is attached to the body by tethering at two points in an annulus around the catheter.

An expandable cage may be joined to the body in a position adapted to disable or hinder the actions of the mitral or tricuspid valve when in use. Preferably, the distal end is joined to a pig tail shaped arrangement to prevent injury to heart during insertion.

The hollow body may include a first and second tubes which are integrally joined and parallel. The second tube may include a number of vent holes, the more distal of which will lie in the ventricular cavity and the more proximal will lie in the atrial cavity.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

DESCRIPTION OF THE INVENTION

Preferred embodiments of the invention will now be described with reference to the accompanying drawings and non-limiting examples.

Figure 1:
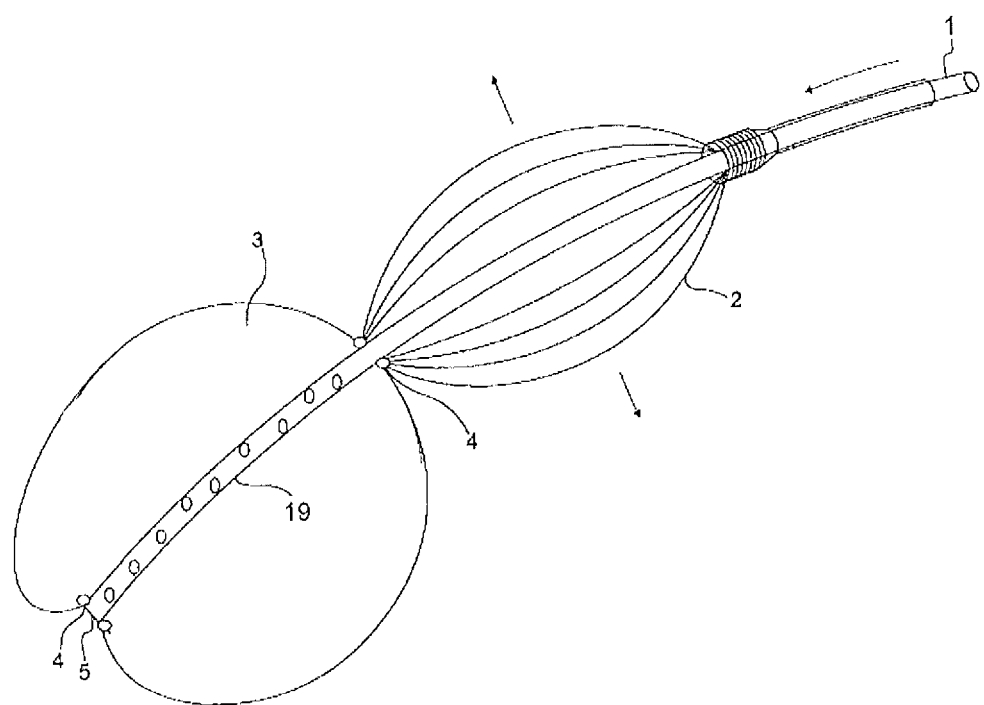
FIG. 1 depicts a cross sectional side view of a first preferred embodiment of the present invention.
Figure 2:
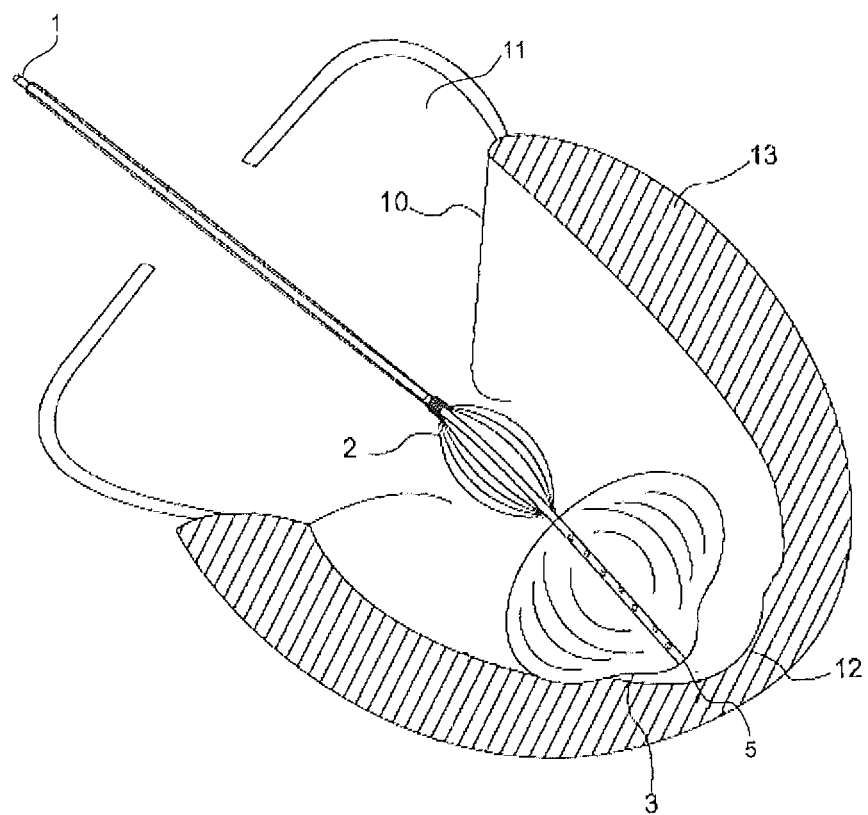
FIG. 2 depicts a cross sectional side view of embodiment shown in FIG. 1 wherein the device or device is positioned within a donor heart.

In a first preferred embodiment of the present invention, the embodiment includes a device and/or system as depicted in FIGS. 1 & 2. The following description makes reference to FIGS. 1 & 2.

The device and/or system may include a catheter or cannula 1 having at least two ends being a operator end (not shown) and a distal end 5. The operator end is adapted for connection to other devices or machines or may be manipulated by surgeons or operators during use. The distal end 5 is adapted for entry in the ventricle 12. In this specification, the term "operators" or "operator" means any person or persons skilled in the art of cardiac surgery and capable of operating said device or system.

FIG. 1 shows part of the first preferred embodiment of the present invention, in particular the region near to the distal end 5.

Preferably, the first preferred embodiment is a device adapted to be received or inserted into a donor heart between explantation and implantation of the transplantation procedure. It is a preferred advantage of the current system or device that it is should be adapted to for cardiac evaluation of the donor heart prior to implantation.

The device may be adapted to not or not significantly damage the heart within which it is inserted.

In this embodiment, the body 1 of the cannula is integrally joined to the distal end 5. The body 1 is preferably hollow and allows for the connection of a pressurising device at the proximal end (not shown). The hollow body allows for fluid to be pumped out of the distal end 5, into the balloon. The body 1 may be constructed of a semi rigid material that includes enough flexibility to allow the cannula to bend around corners during insertion either through the vena cava (to right ventricle) or left atrium (to left ventricle). The cannula is rigid enough to allow for cannula not to collapse or buckle when lateral force is being applied by a surgeon at the proximal end during insertion.

The distal end 5 preferably includes an end wherein the balloon is configured so as to extend past the tip when the balloon is inflated. Preferably, the balloon may be adapted to inflate or extend past the furthest point of the distal end of the cannula and thereby effectively positioning the balloon between the distal end and the heart to act as a cushion in a beating heart. This may prevent the distal end from damaging the interior of the heart or blood vessels. Preferably, the balloon would only be required to be partially inflated to effect this feature, or there would be another, smaller balloon for this cushioning purpose, with its own lumen up the cannula 1.

Figure 7:
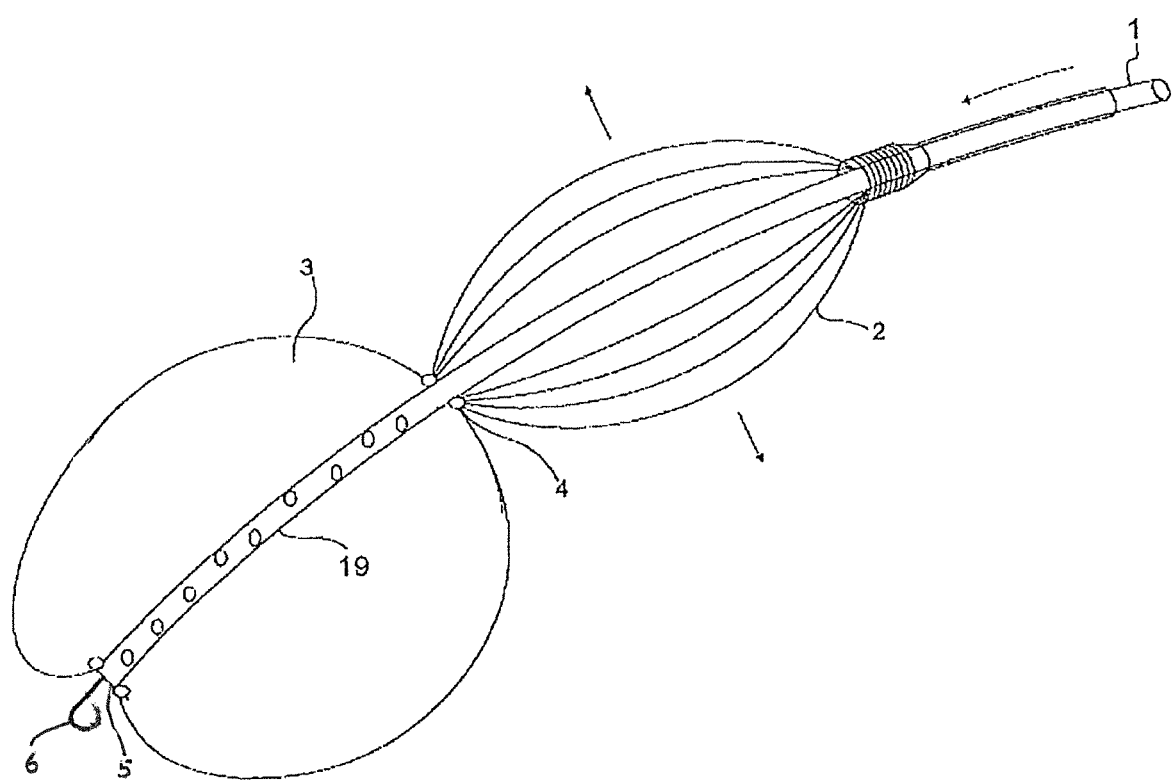
FIG. 7 depicts a cross sectional side view of the device shown in FIG. 1 with a pig tail arrangement.

Alternately, as shown in FIG. 7, a pig tail arrangement 6 may be attached to the distal end 5. The pig tail arrangement 6 is a curved extension integrally moulded to the distal end 5, which is shaped similar to a pig's curled tail. The advantage of the pig tail arrangement 6 is it may prevent laceration or tearing or other injury to heart or blood vessels during insertion as it spreads the force at the distal end 5 if the said end contacts a blood vessel wall or heart wall during insertion. Additionally, the pig tail arrangement 6 is configured to be more flexible than the body 1 and therefore it will collapse and bend over before the body 1 punctures a blood vessel or before the body collapses or crimps, preventing its function.

The device includes an inflatable balloon 3 mounted proximal to the distal end 5 along the body 1. The balloon is fixed in place with tethering 4 or stitching which prevents or limits the movement of the balloon 3. Preferably, the balloon is constructed of a flexible and elastic material that may be inflated when pressure is applied to the interior of the balloon 5 by way of pressure received from body 1. The pressure exits the body 1 through balloon vent holes 19 in FIG. 3 and enters the balloon 3. In this embodiment, when pressure is decreased or removed the balloon may deflate into a collapsed position for insertion. When in use, the balloon is inflated by the aforementioned means.

Adjacent to the balloon 3 on the proximal side of body 1 is attached an expandable mesh or cage 2. Preferably, the cage 2 is selectively able to expand or contract when desired by a surgeon. The cage 2 may be attached the tethering 4 which may also be connected to further tethers which are operable by surgeons or doctors at the proximal end of the cannula 1 using a sliding sleeve. The cage 2 may be constructed of a biocompatible alloy including titanium, stainless steel or nitinol or from a polymer.

The sliding sleeve preferably engages the cage 2 at an end opposite to the end attached to the base of the balloon. The sleeve may surround a portion of the cannula with a cylinder that comprises internal diameter greater than the outer diameter of the cannula. Preferably, the surgeon may slide the sleeve away from the surgeon which then exerts a force on the cage 2. Preferably the cage 2 comprises a series of parallel struts and as the sleeve is slid towards the balloon. The struts bend and expand to cage 2 into an expanded configuration. When the sleeve is slid towards the surgeon, the struts are relaxed and change position so that they flatten against the outer surface of the cannula and this is the deflated configuration of the cage 2.

Preferably, the struts may be made of flexible and resilient material that is adapted to be bent or deformed in accordance with hand pressure applied by the surgeon to the sleeve.

FIG. 2 depicts the first preferred embodiment of the present invention in situ or in use, wherein the distal end 5 of the cannula 1 has been inserted into a ventricle 12 of a heart 13. The view shown in FIG. 2 is a stylised illustration of the heart 13.

Figure 5:
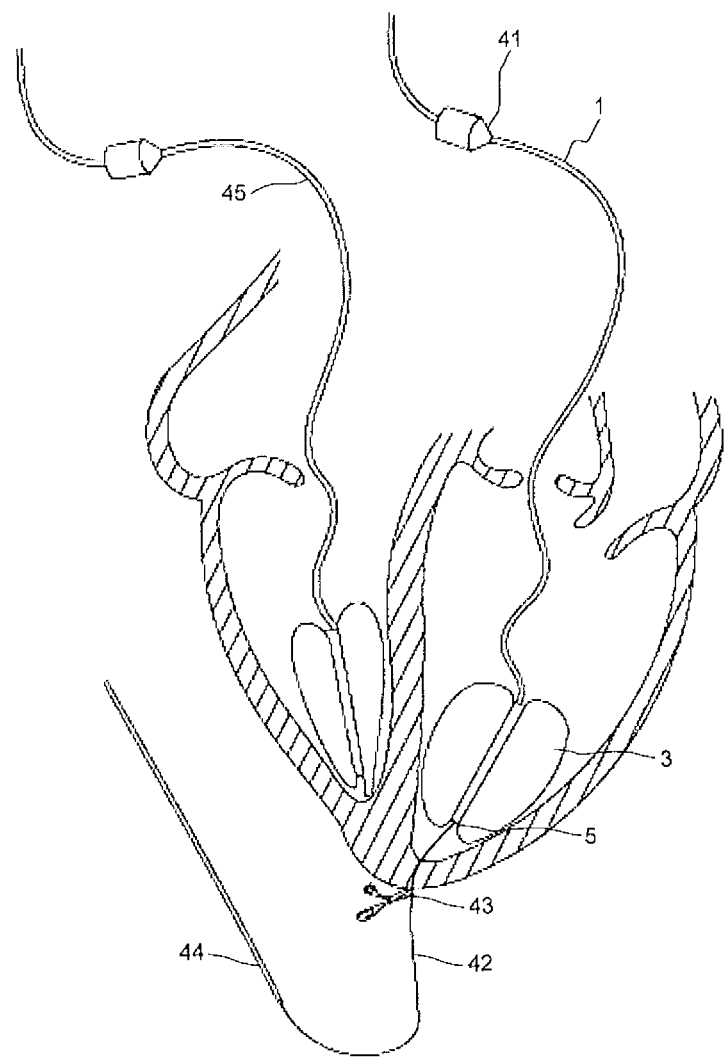
FIG. 5 depicts a cross-sectional side view of a further preferred embodiment of the present invention.

During insertion of the first preferred embodiment, the cannula inserted through a blood vessel into the left atrium of the heart 13. The cannula is then positioned through the mitral valve 10 and secured into the left ventricle 12 or through the tricuspid valve and secured in the right ventricle (FIG. 5).

Initially during the insertion procedure, the balloon 3 is in a collapsed position and when the final position is reached by the surgeon, the balloon 3 is inflated by applying an incompressible fluid pressure along the cannula body 1 into the balloon 3. FIG. 2 depicts the balloon in an inflated configuration.

Preferably, the balloon 3 is constructed so that it may include maximum expansion limit. The limitation on inflation may allow the balloon 3 not to be over inflated which may damage the left ventricle. Alternatively, ribbing along the surface of the balloon 3 may significantly reduce the elasticity of the balloon.

In use, the cage 2 is expanded by the surgeon using tethering to expand the cage across the mitral valve 10 to ensure that the mitral valve 10 remains in the open position.

The insertion of the cannula 1 may serve several functions. The first preferred function is that the hollow body 1 of the cannula 1 may be connected to a pressure sensor (not shown), wherein the pressure sensor may sense fluctuations of pressure acting on the body and the balloon. A controller device electrically connected to the pressure sensor may calculate the difference between the applied pressure (which the surgeon or operator applied) to the pressure being experienced by the balloon 3 and body 1. This difference will be mainly due to the pulsed actions of the heart contracting, thereby allowing for surgeons to detect and measure the viability and strength of a donor heart. This system and device may be used in vivo or in vitro depending on the stage of the transplant operation.

Figure 3:
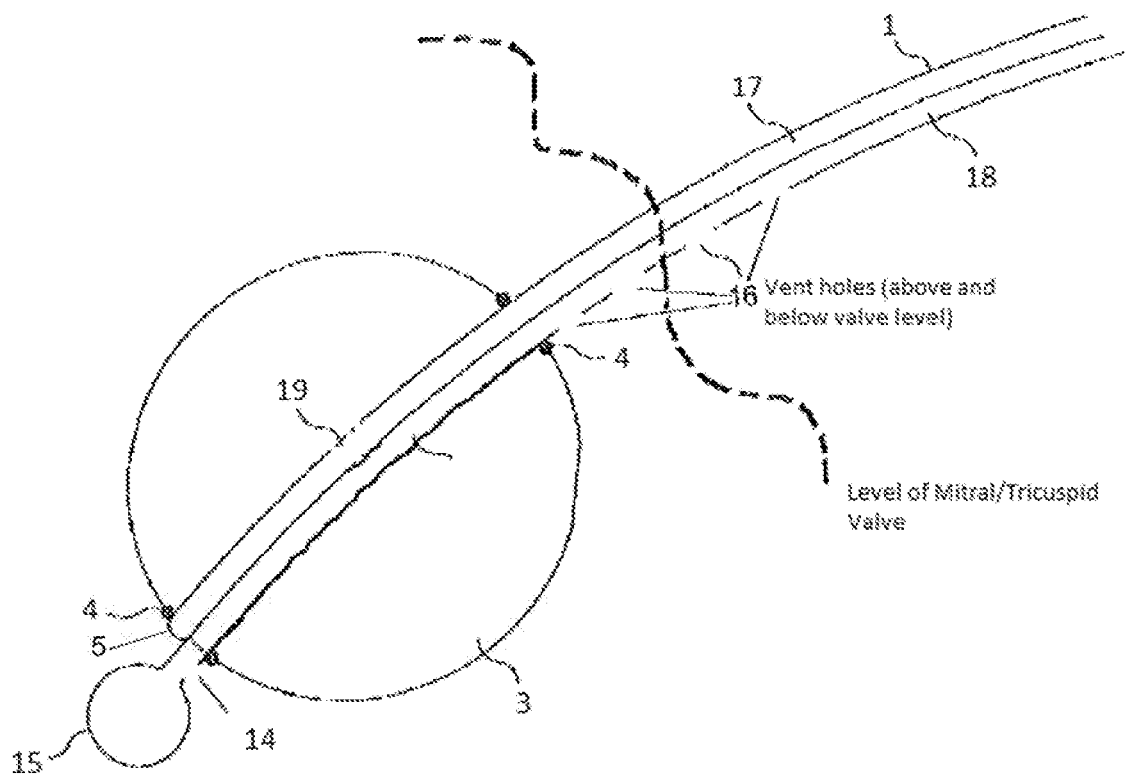
FIG. 3 depicts a cross-sectional side view of a second preferred embodiment of the present invention.

FIG. 3 depicts a variant design of the embodiment shown in FIGS. 1 & 2. This further preferred embodiment shown in FIG. 3 is labelled as the second preferred embodiment of the present invention.

Preferably, the second preferred embodiment lacks a cage 2 but the balloon 3 may be secured by inflation and the inflation force pushing against the walls of the left ventricle may suffice to secure the balloon in place.

The pig tail arrangement 6 at the distal end 5 (FIG. 7) may be replaced with a relatively soft bulb 15, to prevent or limit trauma, as shown in FIG. 3.

The body 1 has been modified to include a bifurcated hollow body with two concentric tubes that may be integrally joined together to form the body 1. The first tube 17 acts as inflation conduit for inflating the balloon 3 through balloon vent holes 19. In this embodiment, the second tube 18 in the body 1 includes a series of vent holes 16 to prevent the left ventricle (when inserted into the left ventricle) from pumping out fluid contents including air through the aortic valve. The second tube 18 includes a second set of balloon vent holes 14 preferably positioned proximal to the distal end 5, wherein the vent holes are adapted to receive fluid of the ventricle and allow it to be vented at mitral valve vent 16. Preferably, vent 16 is mounted and positioned across the mitral valve so as prevent flow from the aortic valve. The second tube 18 also includes mitral valve vent 16, wherein this vent is positioned along the length of the body 1 to be in a position near the mitral valve in the left atrium, when inserted. The second tube 18 is not in fluid communication with the first tube 17.

Preferably, mitral valve vent 16 may be used to selectively open or close the mitral valve 10. The embodiment shown in FIG. 4 may also be applied to the right ventricle, in which case, the mitral valve references would be replaced the tricuspid valve.

Figure 4:
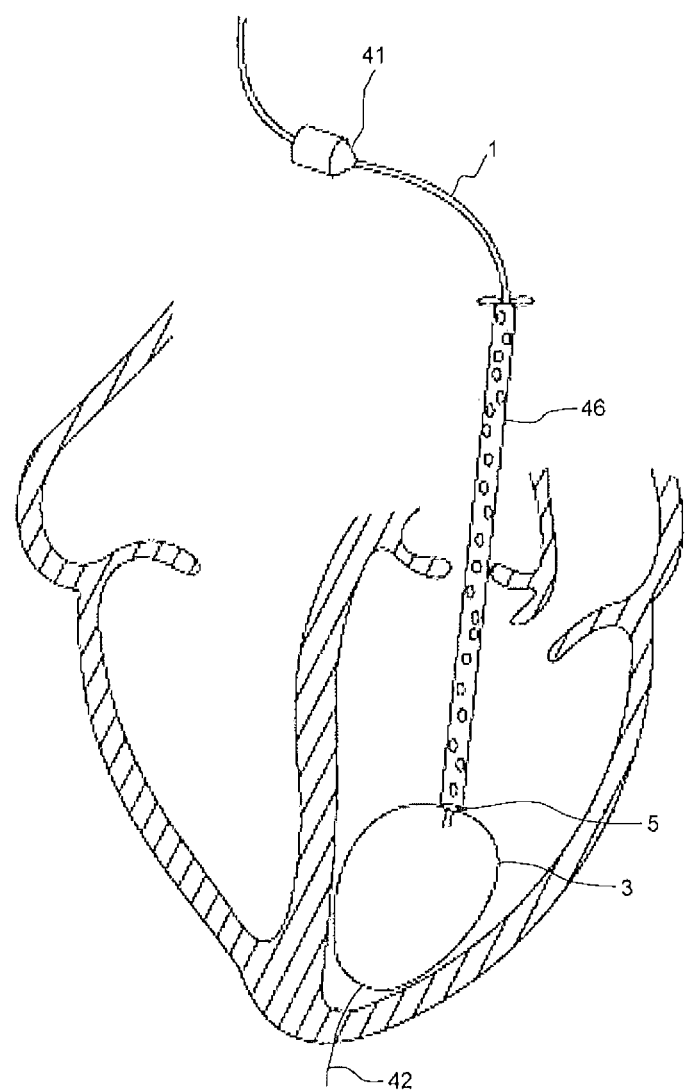
FIG. 4 depicts a cross-sectional side view of a further preferred embodiment of the present invention.

FIG. 4, depicts a further embodiment of the present invention, wherein the balloon catheter or cannula has been inserted within the apex of the left ventricle. In this embodiment, the relatively stiff shaft 46 or body of the cannula has been inserted within the left ventricle. The distal end 5 of the cannula 1 has been sewn or stitched 42 to the apex of the left ventricle to prevent or limit the possibility of the ejection of the balloon or cannula during implantation.

Preferably, the stitching extends from the distal end or tip of the cannula through the interior wall or myocardium tissue of the heart and extends out through the exterior wall of the ventricle.

Preferably, the device or cannula shown in FIG. 4 also includes a series of holes or vents positioned along the body of the cannula Preferably, the stitching may be secured by a spring clip (shown in FIG. 5 as clip 43) positioned on the outside of the heart proximal to and adjacent to the apex of the left ventricle. This feature is shown and depicted in FIG. 5. The stitching may also be secured by a knot tied by the surgeon.

FIG. 4 shows a configuration wherein the balloon is mounted or positioned on the distal end 5 of the cannula. In this case, the heart is protected from the distal end of the cannula, however other alternate versions could be configured wherein the balloon 3 is mounted around the distal end or positioned on the end of the distal end 5.

Alternately, for configurations such as the one shown in FIG. 4 wherein the balloon is attached the end of the distal end. It may be preferred to a mount a further reinforcement pad on the surface of the balloon to allow for the connection of stitching or tethering. The reinforcing pad is preferably constructed of a soft padding material that is adapted to receive needles or stitching.

Further, FIG. 5 shows and depicts further uses and adaptation of the preferred embodiments wherein two cannulae have been simultaneously implanted. A first cannula 1 has been inserted within the left ventricle of the heart and a second cannula 45 has been inserted within the right ventricle.

FIG. 5 also shows and depicts the insertion needle used to complete the stitching of the thread or tether which connects the apex of the respective ventricle to the distal end of the respective cannula. The combination of the needle 44 and tether 42 connected to the balloon may be sufficient to reposition the balloon within the apex of the ventricle, if the tether is pulled tight. This method of securing the balloon at the distal end of the cannula may assist surgeons to implant devices wherein the balloon is very floppy and has a tendency to collapse on itself during the implantation.

Figure 6:
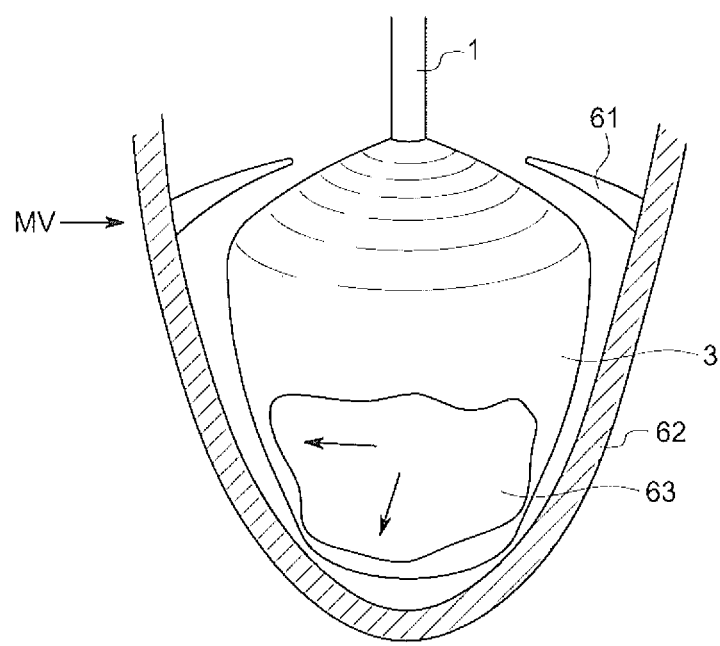
FIG. 6 depicts a cross-sectional side view of a further preferred embodiment of the present invention.

Preferably, in the embodiments depicted in FIGS. 4 & 5, these embodiments may also include pressure transducers 41 attached to cannula at some predetermined distance from the heart. Preferably, these pressure transducers may be used to measure pressure within the hollow cannula body and measure pressure being exerted on the balloon at the distal end. These measurements may lead to data being acquired that describes the functioning or strength of the ventricle compressions against the balloon. Thereby this data may be logged or sent to a controller system In a further embodiment of the present invention as depicted in FIG. 6, cannula 1 is provided with an inflatable balloon tip 3. The balloon tip is preferably inflated within a ventricle 62 to occupy the full volume or close to the full volume of the ventricle. Preferably, the balloon tip is adapted to be shaped to the ventricle wherein the upper portions of the balloon extend away from the central longitudinal axis of the cannula at a greater angle than the lower portion of the balloon. The lower portion extends down to the distal end of the cannula and forming a rounded end on the actual tip. The balloon is preferably formed of both the upper and lower portions integrally joined and sealed together. The lower portion is generally conical shaped with a rounded distal end.

Preferably, the upper region of the balloon is stiffer and less flexible than the lower portion to allow the lower portion to move and fill the ventricle. Preferably the upper surface of the balloon may have a same or similar maximum diameter as the diameter of the upper interior surface of the ventricle as shown in FIG. 6.

Preferably, the balloon is generally ventricle shaped but preferably with a dimple (like the shape of two soft knuckles) at the distal end to prevent the end of the shaft contacting the ventricle and damaging it (shown in FIG. 5 on the bottom of the balloons)

Preferably the balloon may include differential gradients of material. The differential gradients allow differential zones of expansion via allowing or constrain the stretching of the balloon about the central axis. More preferably, the balloon may be more stretchable in a radial direction, and this may prevent ingress or herniation back up into the above positioned atrium. Preferably, the outer surface of the balloon may include a partial textured surface which may allow selected regions of the balloon to grip the inner wall of ventricle better than non-textured regions. Additionally, the textured surfaces may be used to reinforce thinner areas of the ventricle to prevent or ameliorate herniation into either atrium.

The preferred differential between flexible and stiff may be structured so that the stiffer regions are positioned proximal to the top of the balloon or upper portion, flexible in the middle, stiff at the bottom where the dimples are preferably positioned (shown in FIG. 5).

Dimple at the distal end of the lower portion of the balloon at the end of the shaft may protect the ventricle from being damaged by tip of the shaft which allows the balloon to expand in chosen directions (e.g. mostly longitudinally along the length of the heart)

Preferably, the balloon cannula shaft 1 in FIGS. 1, 2, 3, and 6 may include a rigid longitudinally but flexible and resilient body in lateral axis (directions are relative to the orientation of the heart). Preferably, the shaft 1 is adapted to allow it some degrees of movement with a beating heart but to help prevent damage to the heart Preferably, the shaft 1, may be selectively fixed in position so to allow it to move in a limited way with the beating heart, but to require it to stay inside the ventricle in order to take measurements.

The preferred embodiment may include an ability to measure pressure using a pressure tip transducer mounted within the balloon.

This sensor may provide high fidelity pressure measurements: to measure dP/dT (allowing use of the whole waveform, but also of the numerics and waveforms of both positive and negative dP/dT, and also dP/dT÷pressure ie. ((dP/dT)/P).

Preferably, the present embodiment may also include a servo controlled inflation device adapted to be connected to the shaft and the balloon. Preferably, the shaft is adapted to be hollow and allows for the pumping of fluid or gas to inflate or deflate the balloon mounted on its distal end. Preferably, the servo controlled inflation device may be attached to the opposed end of the shaft 1 relative to the balloon 3. Preferably, the servo controlled inflation device may allow for the controlled electric inflation of balloon, possibly by way of a piston shuttle, or pump, or controlled release of pressurised gas, for example via a proportional solenoid controlled valve. Other pumping mechanisms are possible including centrifugal pumps. The inflation device may also selectively allow for the deflation of the balloon. Preferably, pressures and volumes within the balloon may be monitored by sensors including pressure sensors in the tip or sensors in the inflation device. Optimal volumes and pressures may be determined experimentally by the surgeon using the system or preferably, the system may be computer controlled wherein hyper extension of the balloon tip into areas not defined by the ventricle is minimised by correct pressure and volume maintenance. The diagnostics measures may also be used and taken by the system:

a. pressures
b. volumes
c. dP/dT, +ve, −ve, ((dP/dT)/P
d. developed pressure
e. measuring the affect of the inflated or working (shuttled) balloon on the ECG measurement
f. temperatures
g. SpO2 sensors on the balloon, cannula shaft, or tip, to measure Oxygen saturation inside the organ, at particular sites as desired
h. ECG electrodes, contact pads, or conductive soft mesh—one or more in or on each of balloon, or connected to a bag which contains the heart which this balloon is measuring, fluid to enable an electric connection for sensing ECG and delivering current to the heart at a site that is determined by the sensing of the signals on these sites, or other measures
i. Measure efficiency of heart–work done/O2 consumed The above measurements may be taken by an array of sensors mounted on 1, or positioned within or proximal to the tip of the balloon.

Preferably, measuring work done by the heart during a pre-set time interval may enable us to also use the consumed $O_2$ measurement to calculate efficiency of heart. Additionally, the use of a piston in the inflation device that is connected to balloon to let liquid drive piston in and out—matching the fluid being pushed out of, then accepted back into the ventricle by the heart may allow for the measurement input and output of O2 in the perfusate or blood whilst doing this to determine the $O_2$ usage over a short time frame—say a minute, as compared to the resting heart $O_2$ consumption, and the consumption change over time and also across measurements.

In this specification, the term "tube" means the same or equivalent as "lumen".

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrially applicable.

CITATION LIST

Bell R M et al. *J. Mol Cell Cardiol*. 2011 June; 50(6):940-50
Suga H, Sagawa S. Circ Res. 1974; 35:117-126
Goto Y et al. Am J Physiol Heart Circ Physiol 1988; 255:H394-H396
Eaton L W et al. Circulation. 1979; 60:320-326

The claims defining the invention are as follows:

1. A device for a cardiac procedure on a heart of a human prior to implantation, said device comprising:
   a first cannula having a hollow tubular body and at least a distal end for insertion into the heart of the human and an operator end adapted for an operator to position the first cannula within a region defined by an interior surface of a ventricular apex and adapted for connection to a fluid pressuring device and a pressure transducer;
   a second cannula having a hollow tubular body joined in parallel with the hollow tubular body of the first cannula, the hollow tubular body of the second cannula comprising a number of holes to vent a ventricle of the heart across a mitral or a tricuspid valve thereof;
   a curved extension joined to the distal end of the first cannula; and
   an inflatable balloon positioned near to the distal end in fluid communication with the hollow tubular body of the first cannula to allow for selected inflation of the balloon;
   wherein the pressure transducer is attached to the first cannula or the balloon;
   wherein the balloon has a differential gradient of material to allow for differential zones of expansion;
   wherein the curved extension is collapsible; and
   wherein the curved extension is relatively more flexible than the hollow tubular body of the first cannula.

2. The device of claim 1, wherein the distal end of the first cannula is adapted to be inserted within the ventricle of the heart.

3. The device of claim 1, wherein pressure data is calculated from a difference of internal pressure applied to the hollow tubular body of the first cannula and the balloon and a pressure applied to an exterior surface of the balloon by an interior pressure of the heart acting on the balloon.

4. The device of claim 3, wherein the pressure data is detected by the pressure transducer, the pressure transducer in communication with the interior of the balloon or hollow tubular body of the first cannula.

5. The device of claim 1, wherein the balloon comprises ribbing along a surface of the balloon to prevent or limit over expansion of the balloon.

6. The device of claim 1, wherein the balloon is attached to the hollow tubular body of the first cannula by tethering.

7. The device of claim 1, wherein an expandable cage is joined to the hollow tubular body of the first cannula in a position adapted to disable or limit the action of the mitral or the tricuspid valve.

8. The device of claim 1, wherein the balloon, when inflated, extends past the farthest point defined by the distal end of the first cannula and wherein the balloon is adapted to prevent injury to the heart during insertion of the device.

9. The device of claim 1, further comprising stitching extending from the distal end of the first cannula, the stitching for securing the distal end of the cannula in position within the ventricle of the heart.

10. The device of claim 1, wherein the curved extension prevents injury to the heart during insertion, the curved extension having a shape of a pig tail.

11. A device for determining cardiac viability, the device comprising:
    a first cannula having a hollow tubular body, the first cannula for insertion into a region of a heart defined by an interior surface of a ventricular apex;
    a second cannula having a hollow tubular body joined in parallel with the hollow tubular body of the first cannula, the hollow tubular body of the second cannula comprising a number of holes to vent a ventricle of the heart across a mitral or a tricuspid valve thereof;

an inflatable balloon attached to the hollow tubular body of the first cannula near a distal end thereof, the inflatable balloon in fluid communication with an interior of the hollow tubular body of the first cannula to allow for selected inflation of the inflatable balloon, the inflatable balloon having a differential gradient of material that allows the inflatable balloon to have differential zones of expansion;

a pressure transducer attached to the first cannula or the balloon;

an expandable cage attached to the hollow tubular body of the first cannula; and a sleeve slidably disposed about the hollow tubular body of the first cannula, the sleeve for expanding the expandable cage when it is slidably moved against the expandable cage.

\* \* \* \* \*